United States Patent [19]

Van Leeuwen et al.

[11] 4,408,078

[45] Oct. 4, 1983

[54] PROCESS FOR THE HYDROFORMYLATION OF OLEFINS

[75] Inventors: Petrus W. N. M. Van Leeuwen; Cornelis F. Roobeek, both of Amsterdam, Netherlands

[73] Assignee: Shell Oil Company, Houston, Tex.

[21] Appl. No.: 399,161

[22] Filed: Jul. 16, 1982

[30] Foreign Application Priority Data

Dec. 23, 1981 [GB] United Kingdom ............... 8138734

[51] Int. Cl.³ ............................................ C07C 45/50
[52] U.S. Cl. ..................................... 568/454; 502/169
[58] Field of Search ............................. 568/454, 909; 252/429 R

[56] References Cited

U.S. PATENT DOCUMENTS

| | | | |
|---|---|---|---|
| 3,876,672 | 4/1975 | Mrowca | 568/454 |
| 3,981,925 | 9/1976 | Schwager et al. | 568/454 |
| 4,013,583 | 3/1977 | Knifton | 568/454 |
| 4,101,565 | 7/1978 | Poist | 568/454 |
| 4,198,352 | 4/1980 | Kim et al. | 568/454 |
| 4,334,042 | 6/1982 | Matsumoto et al. | 568/454 |
| 4,370,258 | 1/1983 | Ogata et al. | 568/454 |

*Primary Examiner*—Werren B. Lone

[57] ABSTRACT

Process for the hydroformylation of olefins with carbon monoxide and hydrogen in the presence of a ligand stabilized, platinum-containing catalytic system comprising at least one secondary phosphine oxide moiety.

18 Claims, No Drawings

PROCESS FOR THE HYDROFORMYLATION OF OLEFINS

FIELD OF THE INVENTION

The present invention relates to a process for the hydroformylation of olefins using a modified Group VIII metal catalyst.

BACKGROUND OF THE INVENTION

The hydroformylation of olefins, i.e. the catalytic addition of carbon monoxide and hydrogen to olefinically unsaturated compounds to produce aldehydes and/or alcohols, is of great industrial importance. Aldehydes, in particular linear aldehydes, are very useful intermediates in industrial practice because of their terminal carbonyl group. For instance, they can be readily reduced to the corresponding primary alcohols and oxidized to the corresponding carboxylic acids. They also undergo addition and/or condensation reactions with a variety of chemicals such as hydrogen cyanide, alcohols, nitroparaffins as well as condensation reactions with themselves and other carbonyl-containing compounds. They can also be reacted with ammonia and derivatives thereof such as primary amines.

Much effort has been devoted over the years to the development of better catalytic systems, especially with a view to improve the linear/branched product ratio since this will have a positive influence on biodegradability problems encountered in various applications wherein aldehydes and/or alcohols are used as intermediates or starting materials, e.g. in surface-active compounds.

Since the classical cobalt carbonyl catalyst system which produces a large amount of branched chain products, more advanced systems have been suggested comprising organophosphorus compounds, in particular tertiary phosphines or phosphites, as ligands, e.g. as disclosed in British Pat. No. 1,138,601.

Not only ligands have been suggested as promoters and/or stabilizers for the original hydroformylation catalysts but, also, certain metal halides. For instance, it is known from U.S. Pat. No. 3,876,672 and No. 4,101,564, respectively, that Group IV A metal halides, in particular tin (II)-halides, preferably also containing a quaternary ammonium halide, can also be applied to improve the linear/branched ratio, especially when platinum is used as the main catalyst.

However, the use of Group IV A halides has the intrinsic drawback that normally a rather large excess of such compound is required which makes the working-up procedure of the process very unattractive. Moreover, it appears that high linear/branched product ratios can only be obtained at the expense of an increasing amount of alkanes being co-produced. It is therefore very desirable to develop a hydroformylation catalyst, which matches the speed of the cobalt-carbonyl based catalyst, while maintaining a high linear/branched product ratio at a minimal co-production of undesired alkanes.

It has now been found that olefins can be hydroformylated with a very low amount of alkanes being co-produced, even at high linearity when the process is carried out in the presence of a specific ligand-stabilized, platinum-containing catalytic system.

SUMMARY OF THE INVENTION

The present invention relates to a process for the hydroformylation of olefins with carbon monoxide and hydrogen in the presence of a ligand-stabilized, platinum-containing catalytic system comprising at least a secondary phosphine oxide moiety. Utilizing the instant catalyst, olefins can be hydroformylated with a very low amount of alkanes being co-produced while maintaining a high linear/branched product ratio.

DESCRIPTION OF THE PREFERRED EMBODIMENTS

Without wishing to be bound to any particular theory, it is thought that the nature of the secondary phosphine oxides, i.e. compounds according to the general formula $R^1R^2P(O)H$, wherein $R^1$ and $R^2$ are as defined hereinafter, having both a direct phosphorus-oxygen and a phosphorus-hydrogen bond, is responsible for the good results obtained. Since it is not clear whether the secondary phosphine oxide is operating as a ligand per se or in the form of the corresponding anion (the proton presumably also taking part in the catalytically active species), the expression "secondary phosphine oxide" as used herein is meant to include both the molecule itself as well as the corresponding secondary phosphine oxide anion, formally thought to be a derivative thereof.

The secondary phosphine oxides can be represented by the general formula $$R^1R^2P(O)H_n \qquad (I)$$

wherein $R^1$ and $R^2$, which may be the same or different, each represents a substituted or unsubstituted alkyl, alkaryl or aralkyl group and $n=0$ or 1. When $n=1$, the compounds according to the general formula (I) may also be referred to as dihydrocarbyl phosphinous acids, whereas the compounds when $n=0$ (i.e. the corresponding anions) may be referred to as dihydrocarbyl phosphinites.

A suitable class of secondary phosphine oxides comprises compounds according to the general formula (I) wherein $R^1$ and $R^2$, which may be the same or different, each represents an alkyl, aryl, alkaryl or aralkyl group having up to 12 carbon atoms and $n=0$ or 1. Examples include dimethyl phosphinous acid, diethyl phosphinous acid, di-t.butyl phosphinous acid, methyl ethyl phosphinous acid, diphenyl phosphinous acid, the di-tolyl phosphinous acids, methyl phenyl phosphinous acid, ethyl phenyl phosphinous acid and the corresponding phosphinites. Preference is given to the use of compounds according to formula (I) wherein both $R^1$ and $R^2$ represent an alkyl or an aryl group having up to 8 carbon atoms such as dimethyl phosphinous acid and diphenyl phosphinous acid and the corresponding phosphinites.

A further class of secondary phosphine oxides which can be used comprises compounds according to the general formula (I) wherein $n=0$ and $R^1$ or $R^2$ represents an alkyl group containing also at least a group $PR^3R^4$ or $P(O)R^5$ wherein $R^3$, $R^4$ and $R^5$, which may be the same or different, each represents an alkyl, aryl, aralkyl or alkaryl group having up to 12 carbon atoms provided that there are at least two carbon atoms between any two phosphours atoms.

Examples of compounds containing a terminal $PR^3R^4$ or $P(O)R^5$ group include 2-(dimethylphosphino)-ethyl phenyl phosphinite, 2-(diphenylphosphino)-ethyl phenyl phosphinite and 2-(diphenylphosphino)-ethyl phenyl phosphinite.

The secondary phosphine oxides may form part of platinum complexes which may be formally represented by the general formula

Pt(H)(R¹R²PO)L₂     (II)

wherein $R^1$ and $R^2$ are as defined hereinbefore and each L represents an organic molecule having at least one nitrogen, phosphorus, arsenic, sulphur or selenium atom, such atom being in such valency state that it possesses a lone pair of electrons. It should be noted that in case the complexes referred to hereinabove would formally contain a ligand according to the general formula (I), another ligand L would be present to satisfy the coordinative requirements of the platinum atom.

Preferably, the group L comprises a tertiary phosphine, arsine or stibine having the general formula $ZR^6R^7R^8$ wherein Z represents a phosphorus, arsenic or antimony moiety and $R^6$, $R^7$ and $R^8$ form together an alkylene moiety. In the event that the alkylene moiety is built up by groups $R^6$, $R^7$ and $R^8$, which are part of different groups L, the result is a bidentate-type ligand having at least two carbon atoms between the constituting Z atoms.

Examples of ligands according to general formula $ZR^6R^7R^8$ are well known in the art. A selection thereof comprises tributyl phosphine, triphenyl phosphine, dimethyl phenyl phosphine, methyl diphenyl phosphine, dimethyl propyl phosphine, the tritolyl phosphines and the corresponding arsines and stibines as well as bidentate-type ligands such as tetramethyl diphosphinoethane, tetramethyl diphosphinopropane, tetraethyl diphosphinoethane, tetrabutyl diphosphinoethane, dimethyl diethyl diphosphinoethane, tetraphenyl diphosphinoethane, tetraperfluorophenyl diphosphinoethane, tetraphenyl diphosphinopropane, tetraphenyl diphosphinobutane, dimethyl diphenyl diphosphinoethane, diethyl diphenyl diphosphinopropane and tetratrolyl diphosphinoethane. Preference is given to the use of tertiary phosphines, in particular triphenyl phosphine. A preferred catalytic system according to the present invention may be represented by the formula

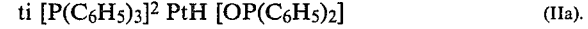

ti [P(C₆H₅)₃]² PtH [OP(C₆H₅)₂]     (IIa).

The secondary phosphine oxides may also form part of platinum complexes which may be formally represented by the general formula

Pt(H)(R¹R²PO)QL$_m$     (III)

wherein $R^1$, $R^2$ and L are as defined hereinbefore, Q represents a hydrocarbyl group having one or two isolated carbon-carbon double bonds and m is 1 or 0 (when Q contains two isolated carbon-carbon double bonds). It should be noted again that in case the complexes referred to as (III) would formally contain a ligand according to the general formula (I) another ligand L would be present to satisfy the coordinative requirements of the platinum atom.

Examples of suitable groups Q comprise lower olefins such as ethylene and propylene as well as non-conjugated dienes, in particular cyclic di-olefins such as 1,5-cyclooctadiene (COD), 1,5-dimethyl-1,5-cyclooctadiene and 1,6-dimethyl-1,5-cyclooctadiene. Preference is given to the use of 1,5-cyclooctadiene.

It is also possible that one or more of the ligands L comprise a substituted organic nitrogen, phosphorus, arsenic, sulphur or selenium compound. Examples of such compounds comprise diphenylphosphino acetic acid, dimethyl- as well as the corresponding and related arsenic and antimony derivatives. Preferance is given to the use of diphenylphosphino acetic acid.

The compounds according to the general formula (II) and (III), which may be the actual catalytically active species or precursors thereof, can be prepared by methods known in the art. One convenient method comprises the reaction between a Pt° compound such as bis(1,5-cyclooctadiene)platinum, represented by the formula Pt(COD)₂ with diphenyl phosphinous acid and triphenyl phosphine, which results in the product [(P(C₆H₅)₃)₂] PtH [OP(C₆H₅)₂]. It is also possible to perform the reaction between the Pt° compound and the secondary phosphine oxide in the presence of a substituted organic phosphoric compound such as diphenylphosphino acetic acid. It depends on the amounts of the various ligands employed a well as their respective coordinative abilities which ligand(s) will eventually be part of the catalytically active platinum compound. It is highly likely that the platinum compound as originally submitted to the reaction will be influenced or even changed because of the presence of both carbon monoxide and hydrogen in the reaction medium.

Another method of preparing a platinum compound according to the general formula (II) or (III) or a precursor thereof, comprises the reaction between a $Pt^{2+}$ compound, for instance, bis(triphenyl phosphine) platinum (II) chloride and an alkaliphosphinite, e.g. sodium diphenyl phosphinite. Depending on the amount of phosphinite applied, one or two of the chlorine atoms will be replaced by the appropriate phosphinite.

The platinum complexes which are used in the process according to the present invention may be prepared as such, for instance, by using the procedures described hereinbefore, or may be prepared in situ from a Pt° complex such as bis(cyclooctadiene) platinum or from the appropriate $Pt^{2+}$ compound, whether or not in the presence of an excess of a ligand according to the general formula L which may or may not form a part of the catalytically active platinum compound.

Examples of olefinically unsaturated compounds which can be readily hydroformylated using a ligand stabilized, platinum-containing catalytic system comprising at least one secondary phosphine oxide moiety include olefins having up to 20 carbon atoms such as alpha-mono-olefins such as ethylene, propylene, butene-1, pentene-1, hexene-1, heptene-1, octene-1, dodecene-1, tetradecene-1, vinylcyclohexane, cyclohexane and cyclooctene; the higher alpha-mono-olefins produced either by thermal cracking of paraffin wax or by the catalyzed oligomerization of ethylene; internal mono-olefins such as pentene-2, hexene-2, hexene-3, heptene-2 and heptene-3; non-conjugated di-olefins such as 1,4-hexadiene and vinylcyclohexene; and aromatic mono-olefins such as styrene, alpha-methyl styrene and isopropenyl benzene. Preference is given to the use of mono-olefins, especially alpha-mono-olefins, since they normally react to a product having a high linearity at an acceptable aldehyde/alcohol ratio at the expense of only a small amount of the corresponding alkene. It has been found that linearities even as high as 70% can be obtained starting from internal mono-olefins such as heptene-2.

The process according to the present invention is carried out under mild process conditions. Temperatures in the range of from about 50° C. to about 180° C. can be suitably applied, but lower or higher temperatures can also be used. Preference is given to temperatures in the range of from about 75° C. to about 125° C. The process according to the present invention can be suitably carried out at pressures up to about 200 bar. Preference is given to pressures in the range of from about 5 to about 140 bar.

The process according to the present invention can be carried out suitably using a molar ratio of carbon monoxide to hydrogen of 1:1, which is the stoichiometric ratio to produce aldehydes. Excess carbon monoxide or hydrogen over the stoichiometric amount as indicated hereinbefore may be present, for instance in a molar ratio between about 12:1 and about 1:12. Good results have been obtained using a carbon monoxide:hydrogen ratio of 1:2.

The amount of the platinum catalyst in the reaction zone, e.g. in the liquid phase relative to the olefin feed is not particularly critical but is preferably chosen so as to maintain a homogeneous liquid medium. In general, higher concentrations of catalytically active species produce a faster reaction rate. Concentration of platinum compounds or complexes in the liquid phase in the range between about $10^{-6}$ moles/liter and about $10^{-1}$ moles/liter can be used. Higher molar concentrations, e.g. of up to about 1 mole/liter are by no means excluded.

The process according to the present invention can be carried out conveniently in the presence of an inert solvent. A variety of solvents can be applied such as ketones, e.g. acetone, methyl ethyl ketone, methyl isobutyl ketone, acetophenone and cyclohexanone; aromatic compounds such as benzene, toluene and the xylenes; halogenated aromatic compounds such as chlorobenzene and orthodichlorobenzene; halogenated paraffinic hydrocarbons such as methylene chloride and carbon tetrachloride; paraffins such as hexane, heptane, methylcyclohexane and isooctane and nitriles such as benzonitrile and acetonitrile. Good results have been obtained using benzene. Also, mixtures of solvents can be suitably applied. It is also possible to use an excess of the starting material as well as of one or more of the appropriate ligands as solvent(s).

When desired, the reaction mixture obtained may be subjected to a catalytic hydrogenation, e.g. over a Raney-Ni catalyst to convert part or all of the aldehyde produced into the corresponding alcohol. The reaction conditions to be applied are well known in the art.

The process according to the present invention can be readily carried out using well-known chemical engineering practice which includes continuous, semi-continuous and batch operation. The reaction time may vary between wide limits, from a couple of minutes to several hours, depending on the specific olefin and catalytic system applied. After the reaction the reaction mixture is worked up by techniques known in the art. The product, aldehyde, can be removed by various means, e.g. by distillation. It is also possible to recycle part or all of the reaction mixture together with the catalytic system.

The invention will now be illustrated by means of the following Examples which are provided as illustrative and are not to be construed as limiting the invention.

EXAMPLE 1

A 100 ml stainless steel autoclave was charged with 20 ml benzene, in which was dissolved 0.1 mmol of compound IIa, which had been prepared by dissolving equimolar amounts of cis-Cl(H)Pt[P($C_6H_5$)$_3$]$_2$, diphenyl phosphine oxide and as a base pyridine in refluxing ethanol. After 30 minutes residual solid impurities were filtered off. Upon standing, white crystals of compound IIa were formed in 70% yield. The autoclave was also charged with 10 mmol of heptene-1. The autoclave was then pressurized with a 2:1 molar mixture of hydrogen and carbon monoxide and heated to 100° C., the pressure in the autoclave now being 45 bar. The autoclave was kept one hour and a half at the reduction temperature of 100° C. and then cooled to ambient temperature. After venting the gases, the reaction product was analyzed using gas-liquid chromatography and nuclear magnetic resonance spectroscopy. The conversion into hydroformylated products amounted to 17.5%, with an aldehyde/alcohol ratio of 0.8. The linearity obtained was 85%, and only 1.2% heptane has been produced.

EXAMPLE 2

The experiment described in the previous Example was repeated using a total pressure of 94 bar. The conversion into hydroformylated products amounted to 15.4%, with an aldehyde/alcohol ratio of 0.5. The linearity obtained was 90%, and only 1.0% of heptane had been produced.

EXAMPLE 3

The experiment described in Example 1 was repeated using a reaction time of one hour and a catalytic system obtained by dissolving 0.1 mmol bis(1,5-cyclooctadiene) platinum, 0.2 mmol diphenyl phosphinous acid and 0.1 mmol diphenylphosphino acetic acid in 20 ml benzene. The conversion into hydroformylated products amounted to 10.1%, with an aldehyde/alcohol ratio of 3.7. The linearity obtained was 90%, and only 1.5% of heptane had been produced.

EXAMPLE 4

The experiment described in the previous Example was repeated using a catalytic system on tetraphenyl diphosphino ethane (0.1 mmol) instead of diphenylphosphino acetic acid. The pressure amounted to 50 bar. The conversion into hydroformylated products amounted to 27.1%, with an aldehyde/alcohol ratio of 8. The linearity obtained was >90%, and only 0.9% heptane had been produced. The reaction rate is of the same order as with the classical cobalt-type hydroformylation catalyst.

EXAMPLE 5

The experiment described in Example 1 was repeated using a reaction time of 17 hours and heptane-2 (10 mmol) as the olefinic feedstock. The conversion into hydroformylated products amounted to 17.5%, with an aldehyde/alcohol ratio of 0.9. A remarkably high linearity of 65% was obtained, and not more than 5.5% heptane had been produced.

EXAMPLE 6

The experiment described in Example 2 was repeated using a reaction time of 5.5 hours and heptene-2 (10 mmol) as the olefinic feedstock. The conversion into hydroformylated products amounted to 24.0%, with an aldehyde/alcohol ratio of 0.5. An even higher linearity was obtained (70%), and not more than 5.0% heptane had been produced.

COMPARATIVE EXAMPLE A

An experiment as described in Example 1 was carried out using only bis(triphenylphosphine) platinum dichloride (0.1 mmol), no secondary phosphine oxide or derivative thereof being present. The autoclave was kept at a total pressure of 30 bar for one hour. Conversion into hydroformylated products was not detected.

COMPARATIVE EXAMPLE B

An experiment as described in Example 1 was carried out using a catalytic system based on bis(triphenylphosphine) platinum dichloride (0.1 mmol) and tin chloride (0.5 mmol) dissolved in acetone. The reaction was carried out for one hour at a pressure of 40 bar. The conversion into hydroformylated products amounted to 26%, with a large aldehyde/alcohol ratio. The linearity was >90%, but heptane had been produced in an amount of 10%.

COMPARATIVE EXAMPLE C

An experiment as described in Example 4 was carried out using triphenyl phosphine oxide (0.2 mmol) instead of diphenyl phosphinous acid (0.1 mmol). The autoclave was kept for one hour at 105° C. and a total pressure of 50 bar. Conversion into hydroformulated products was not detected.

We claim:

1. A process for the hydroformylation of olefins having carbon numbers up to 20 carbon atoms to aldehydes and alcohols which process comprises contacting at a temperature ranging from about 50° C. to about 180° C. and a pressure of up to about 200 bar said olefins with carbon monoxide and hydrogen in a molar ratio between about 12:1 to about 1:12 in the presence of a ligand-stabilized, platinum-containing catalytic system comprising at least one secondary phosphine moiety.

2. The process according to claim 1, which comprises the use of secondary phosphine oxides according to the general formula $R^1R^2P(O)H_n$ (I) wherein $R^1$ and $R^2$, which may be the same or different, each represents a substituted or unsubstituted alkyl, aryl, alkaryl or aralkyl group and n is 0 or 1.

3. The process according to claim 2, which comprises the use of compounds according to the general formula (I) wherein $R^1$ and $R^2$, which may be the same or different, each represents an alkyl, aryl, alkaryl or aralkyl group having up to 12 carbon atoms and n is 0 or 1.

4. The process according to claim 3, which comprises the use of compounds according to the general formula (I) wherein $R^1$ and $R^2$ both represent an alkyl or an aryl group having up to 8 carbon atoms.

5. The process according to claim 4, which comprises the use of compounds according to the general formula (I) wherein said compounds are selected from dimethyl phosphinous acid and diphenyl phosphinous acid and the corresponding phosphinites.

6. The process according to claim 2, which comprises the use of compounds according to the general formula (I) wherein n is 0 and $R^1$ and $R^2$ represent an alkyl group containing, also, at least a group $PR^3R^4$ or $P(O)R^5$ wherein $R^3$, $R^4$ and $R^5$, which may be the same or different, each represents an alkyl, aryl, aralkyl or alkaryl group provided that there are at least two carbon atoms between any two phosphorus atoms.

7. The process according to claim 2, which comprises the use of platinum complexes, which may be formally represented by the general formula $$Pt(H)(R^1R^2PO)L_2 \qquad (II)$$

wherein $R^1$ and $R^2$ are as defined hereinbefore and each L represents an organic molecule having at least one nitrogen, phosphorus, arsenic, sulphur or selenium atom, being in such valency state that it possesses a lone pair of electrons.

8. The process according to claim 7, which comprises the use of a group L having the general formula $ZR^6R^7R^8$ wherein Z represents a phosphorus, arsenic or antimony moiety and $R^6$, $R^7$ and $R^8$, which may be the same or different, each represents an alkyl, alkaryl or aralkyl group having up to 20 carbon atoms or any two of $R^6$, $R^7$ and $R^8$ form together an alkylene moiety.

9. The process according to claims 7 or 8, which comprises the use of a compound according to the general formula II wherein $R^1$ and $R^2$ are as defined hereinbefore and L represents a tertiary phosphine.

10. The process according to claims 7 or 8, which comprises the use of a compound represented by the formula $[P(C_6H_5)_3]_2 PtH [OP(C_6H_5)_2]$.

11. The process according to claim 2, which comprises the use of platinum complexes which may be formally represented by the general formula $$Pt(H)(R^1R^2PO)QL_m \qquad (III)$$

wherein $R^1$, $R^2$ and L are as defined hereinbefore, Q represents a hydrocarbyl group having one or two isolated carbon-carbon double bonds and m is 1 or 0 (when Q contains two isolated carbon-carbon double bonds).

12. The process according to claim 11, which comprises the use of a compound which may be formally represented by the general formula (III) wherein $R^1$ and $R^2$ are as defined hereinbefore, m is 0 and Q represents 1,5-cyclooctadiene.

13. The process according to claim 1, which comprises the use of an alpha-mono-olefin as starting material.

14. The process according to claim 1, which comprises carrying out the reaction at a temperature in the range of from about 75° C. to about 125° C.

15. The process according to claim 1, which comprises carrying out the process at a pressure in the range of from about 5 to about 140 bar.

16. The process according to claims 1, 2, 6, 7, 8 or 11, which comprises the use of a platinum compound or complex in the liquid phase in a concentration in the range of from $10^{-6}$ moles/liter to $10^{-1}$ moles/liter.

17. The process according to claim 1, which comprises the use of an inert solvent.

18. The process according to claim 17 wherein the inert solvent is selected from a ketone, a halogenating paraffinic hydrocarbon, a paraffin or a nitrile.

* * * * *